United States Patent
Adam

(10) Patent No.: US 11,097,991 B1
(45) Date of Patent: Aug. 24, 2021

(54) PHOSPHORUS FERTILIZER BIO-CATALYST FOR SUSTAINABLE CROP PRODUCTION

(71) Applicant: Nadia Adam, Mishawaka, IN (US)

(72) Inventor: Nadia Adam, Mishawaka, IN (US)

(73) Assignee: Biomineral Systems LLC, South Bend, IN (US)

( * ) Notice: Subject to any disclaimer, the term of this patent is extended or adjusted under 35 U.S.C. 154(b) by 0 days.

(21) Appl. No.: 16/689,092

(22) Filed: Nov. 20, 2019

Related U.S. Application Data

(62) Division of application No. 14/578,489, filed on Dec. 22, 2014, now Pat. No. 10,851,027.

(51) Int. Cl.
| | |
|---|---|
| *C12N 1/20* | (2006.01) |
| *C05F 11/08* | (2006.01) |
| *C12N 9/16* | (2006.01) |
| *C12R 1/01* | (2006.01) |

(52) U.S. Cl.
CPC .............. *C05F 11/08* (2013.01); *C12N 1/205* (2021.05); *C12N 9/16* (2013.01); *C12Y 301/03001* (2013.01); *C12R 2001/01* (2021.05)

(58) Field of Classification Search
None
See application file for complete search history.

(56) References Cited

U.S. PATENT DOCUMENTS 8,796,179 B2 * 8/2014 Levenfors ................ C12N 1/20
504/116.1

OTHER PUBLICATIONS

Sang Hye Ji et al. "Isolation and characterization of plant growth promoting endophytic diazotrophic bacteria from Korean rice cultivars". Microbiological Research 169 (2014), pp. 83-98.*

* cited by examiner

*Primary Examiner* — Vera Afremova

(57) ABSTRACT

Endophytic microbial strains as biocatalysts isolated from fresh plant samples, compositions, and methods of use thereof to enhance the growth and/or yield of a plant in the presence of reduced synthetic phosphate fertilizers are provided. Endophytic microbial strains serve as biocatalysts to solubilize mineral-P and mineralize organic-P otherwise unavailable to plants for their nutritional phosphate needs. Thus defined, biocatalysts, will serve to replace synthetic phosphate fertilizers. Also provided are materials and methods for inoculating plants with these biocatalysts at carefully selected inoculum densities to reliably reduce the amount of synthetic phosphate fertilizer by 50% thus accomplishing obtaining optimal yields in technically and cost-effective manner.

13 Claims, 12 Drawing Sheets

Drawings

PHOSPHORUS FERTILIZER BIO-CATALYST FOR SUSTAINABLE CROP PRODUCTION

FIELD OF THE INVENTION

The present invention relates to the field of sustainable agriculture. Specifically, the disclosure provides novel purified bacterial populations comprising plant isolated endophytes and synthetic combinations of seeds with heterologously plant derived endophytes to provide a specific benefit that of optimal production of crop plants in the absence of synthetic phosphate fertilizers or in the presence of synthetic phosphate fertilizers applied at the rate of 30-50% less than the recommended phosphorus fertilizer application rate. In particular, the synthetic compositions and methods disclosed herein are useful for enhancing plant growth in the complete absence of synthetic phosphate fertilizers or in their much reduced presence.

BACKGROUND OF THE INVENTION

The United States is, by far, the largest producer of corn in the world, producing as much as 35% of world's corn, 33% of world's soybean, more than 65% of world's sorghum and is the biggest wheat exporter (Ag 101, US EPA).

Although US currently leads the world in corn production, the portion of agricultural revenue returned to farmers decreased from 37% to 19% from 1950 to 2002 (Atwell et at, 20111). In addition, input costs increased sevenfold and the real price of corn adjusted for inflation decreased fivefold (Duffy, 206).

One major contributor to the input costs is the cost of fertilizer and pesticides because US farming is fertilizer and pesticide intensive.

The cost of phosphate fertilizer has risen steadily from the year, 2000 doubling in the year 2007 (Olcyzk et al., 2007).

Phosphorus fertilizer manufactured from phosphorus rock is mined in the US (Florida), China, Morocco, and Russia. In year 2006 alone, 142 million tons was mined worldwide (Olcyzk et al. 2007), yet, at the current world-wide rate of application of fertilizers, the readily available sources of high grade phosphate rocks will be depleted within the next 60 to 90 years (Runge-Metzger, 1995).

The situation is critical because the supply of phosphate rock in Florida may be exhausted as early as year 2040 according to the Institute of Phosphate Research (Olcyzk et al., 2007).

Phosphate fertilizers have been critical to crop growth because phosphorus deficiency often limits plant growth (Schachtman, et al. 1998; Vance, et al., 2003; Raghothama, and Karthikeyan, 2005) although this essential plant macronutrient is critically important for improving soil fertility in both tropical and temperate regions (Von Uexkûll & Mutert. 1995).

The practice of applying chemical (inorganic) P fertilizers to alleviate P deficiency is inefficient for both logistical and economic reasons however, because 75-90% of soluble P from fertilizers rapidly becomes immobilized as Fe-, Al-, or Ca—$PO_4$ phases in soils (Gyaneshwar et al., 2002).

Thus effective means for utilizing residual accumulated insoluble P in soils and a means for increasing efficiency of applied synthetic P fertilizers are critically needed.

This takes on particular significance when we note that global food production needs to increase by 50% in the next 20 years to sustain the increasing world population and prosperity.

Although theoretical estimates have suggested that the accumulated P in agricultural soils is sufficient to sustain maximum crop yields worldwide for about 100 years (Gyaneshwar et al., 202), most soils are deficient in bioavailable P.

Therefore, sustainable alternatives to improving P bioavailability are needed for maintaining U.S.'s edge in crop production and agricultural productivity in general.

The proposed embodiment will address the current need for sustainable and cost efficient P management in soils by developing a biocatalyst that makes mineral soil-P, and organic-P available for plant needs thus reducing or eliminating the need for the application of synthetic P fertilizers by a combination of utilization of already available soil-P and by increasing the efficiency of applied synthetic-P fertilizer.

The proposed embodiment will have the additional benefit of improving surface and ground water quality because application of manures and fertilizers has resulted in increased transfer of soil P (solid associated) to solution and eventually, via erosion and runoff, to surface waters where it plays a key role in eutrophication and impairment of affected waters as a resource for drinking, recreation and industry.

The total soil P content typically varies between 500 and 2000 mg $kg^{-1}$ (Vance et al., 20113).

Of this, typically 30-50% of the total insoluble P is present as organic P ($P_o$) mainly as inositol phosphate and the remaining is found as Fe-, Al- or Ca-associated mineral phosphate ($P_i$); phosphate dissolved in soil solution ranges between only 0.1 and 10 µM (Bielski, 1973; Ozanne, 1980; Raghothama, 1999; Frossard et al., 2000).

Because plants can only take up phosphorus as dissolved $H_xPO_4^{y-}$ ions, and for optimal crop growth 0.5-0.7 mM dissolved P is needed in the soil solution, most soils are P deficient and crop growth is often limited by P bioavailability.

Application of chemical fertilizers i.e., phosphate salts is used to supplement the limited pools of dissolved P; however, because of high affinity of P binding to Fe-oxyhydroxide. Al-oxyhydoxide minerals and precipitation as calcium-phosphate phases, dissolved P is quickly converted to insoluble P.

The main goal of the preferred embodiment then is to increase the efficacy of chemical fertilizers and to use the already existing substantial reserves of insoluble soil-P, thereby reducing the application of chemical fertilizers.

Toward this goal, we enhance dominant natural mechanisms of insoluble soil-P bioavailability.

Two main mechanisms of making Pi and Po bioavailable for plant's nutritional needs involves secretion of organic acids to solubilize Pi and secretion of phosphatase enzymes for mineralization of Po. These organic acids and phosphatase enzymes are secreted both by soil microorganisms (bacteria and fungi) and to a smaller extent by plant roots in response to P deficiency (Raghothama and Karthikeyan, 2005; Martinez, 1967).

Although both bacteria, and fungi are ubiquitous in soils, P solubilizing and Po mineralizing bacteria (phosphobacteria) generally outnumber their fungal counterparts by 2-150 fold (Hilda and Fraga, 1999); the P solubilization potential of phosphobacteria can therefore be enhanced to serve as an effective biocatalyst in making insoluble 'fixed' P plant available in an eco-friendly, reliable and sustainable manner.

Phosphobacteria have both epiphytic and endophytic modes of association with the host plant (corn, soybean, wheat, and sorghum, and other crops by extension) and the mode of association can affect the efficacy of phosphobacteria.

Colonizing the plant root epiphytically is difficult because the inoculant has to compete with the native soil bacteria (Kozyrovska et al., 1996).

Phosphobacteria with endophytic relationship with host plant reside within apoplastic spaces inside the host plant thus keeping them away from the natural biocenosis giving them a significant edge in competing with the soil bacteria (Kozyrovska et al. 0.1996; Sturz et al., 20011).

Because, endophytes live within the plant, they can recover more easily from stress situation; they may also form beneficial host-endophyte allelopathies thus protecting the plant from superinfection by soil bacteria (Kozyrovska et al., 1996; Sturz et al., 2010).

SUMMARY OF THE INVENTION

The proposed embodiment pertains to the development of biofertilizer consisting of endophytic phosphobacteria (Bio-Cat-P) inoculated crop seeds as an environmentally sustainable, and cost-effective alternative to synthetic fertilizers and/or applied in combination with the synthetic-P fertilizers as a means of increasing the efficacy of synthetic fertilizers. The present invention relates to the field of sustainable agriculture. Specifically, the disclosure provides microbial compositions and methods useful for the optimal production of crop plants in the absence of synthetic phosphate fertilizers or in the presence of synthetic phosphate fertilizers applied at the rate of 30-50% less than needed. In particular, the compositions and methods disclosed herein are useful for enhancing plant growth in the complete absence of synthetic phosphate fertilizers or in their much reduced presence.

LIST OF REFERENCES

Atwell R. C., Schulte L. A., Westphal L. M., How to build multifunctional agricultural landscapes in the US Corn Belt: Add perennials and partnerships, Land Use Policy, 27 (2010) 1082-1090.

Bieleski, R. L., Phosphate pools, phosphate transport, and phosphate availability, Ann. Rev. Plant Physiol. 24 (1973) 225-252.

Frossard E., Condron L. M., Oberson A., Sinaj S., and Fardeau J. C., Processes governing phosphorus availability in temperate soils., J. Environ. Qual. 29 (2000), 12-53.

Gyaneshwar, P., Kumar, G. N., Parekh, L. J., and Poole, P. S., Role of soil microorganisms in improving P nutrition of plants. Plant and Soil 245 (2002) 83-93.

Hilda R. and Fraga R., Phosphate solubilising bacteria and their role in plant growth promotion. Biotechnology Advances 17 (1999) 319-339.

Kozyrovska, N., Kovtunovych, G., and Groosova, E. Kuharchuk, P., and Kordyum, V., Novel inoculants for an environmentally-friendly crop production. Resources Conservation and Recycling, 18 (1996) 79-85.

Martinez, J. R., Organic phosphorus mineralization and phosphatase activity, Folia Microbiologica, 13 (1967) 161-&

Olczyk, T., Yuncong, L., Edward, E., Na-Lampag, S., and Fan, X., 2007. Updates on Fertilizer prices. University of Florida IFAS.

Ozanne P. G., 1980 Phosphate nutrition of plants—general treatise. In The role of phosphorus in agriculture. Eds. F E Khasawneh, E C Sample and E J Kamprath. pp. 559-589. American Society of Agronomy, Crop Science Society of America, Soil Science Society of America, Madison, Wis., USA.

Raghothama K. G., Phosphate acquisition. Ann. Rev. Plant Physiol. Mol. Biol. 50 (1999) 665-693.

Raghothama, K. G. and Karthikeyan, A. S. Phosphate acquisition, Plant Soil 274 (2005) 37-49.

Runge-Metzger, A., 1995, Closing the cycle: Obstacles to efficient P management for improved global food security. In Phosphorus in the Global Environment: Transfers, cycles and Management. Ed. H Tiessen. pp. 27-42. John Wiley and Sons, NY.

Schachtman, D. P., Reid, R. J., Ayling, S. M., Phosphorus uptake by plants from soil to cell, Plant Physiol. 116 (1998) 447-453.

Sturz, A. V, Christie, B. R., Nowak, J., Bacterial endophytes: Potential role in developing sustainable systems of crop production, Critical reviews in plant sciences, 19 (2000) 1-30.

Vance, C. P., Uhde-Stone, C., Allan, D. L., Phosphorus acquisition and use: critical adaptations by plants for securing a nonrenewable resource, New Phytol. 157 (2003) 423-447.

Von Uexküll H. R., Mutert, E., 1995. Global extent, development and economic-impact of acid soils. Plant and soil 171 (1995) 1-15.

DETAILED DESCRIPTION OF PREFERRED EMBODIMENTS

As part of our invention, we isolated and purified a number of endophytic bacteria from corn, sorghum and sugarcane plant parts. All the isolated and purified bacterial strains were screened quantitatively for their ability to function as endophytic phosphobacteria. This was accomplished by screening for production of organic acids for solubilizing inorganic/mineral phosphorus; and for the production of acid and alkaline phosphatase enzymes for conversion of organic phosphorus to inorganic phosphorus. In addition, phosphobacteria were tested for heterologous inoculation of corn and sorghum seeds.

We were able to purify 12 bacterial strains of endophytic phosphobacteria from corn, sorghum, and sugarcane plants of which only one strain T6 showed production of all three extracellular enzymes for phosphorus solubilization that include organic acids, acid phosphatase, and alkaline phosphatase enzymes. This strain has been deposited as BMS-201 with the NRRL and has the accession number B-67827.

The preferred embodiment comprising synthetic combination of the purified bacterial strain T6 (NRRL accession number B-67827) when tested for its heterologous inoculation of corn and sorghum seeds showed excellent inoculation ability without harming the plant. The preferred embodiment comprising synthetic combination of the purified bacterial strain T6 heterologously inoculated corn and sorghum seeds were evaluated in crop systems in hydroponic, simulated soil systems, and real soils.

The preferred embodiment has included isolation of Pi solubilizing and acid- and alkaline-phosphatase producing endophytic bacteria from plant samples of corn, sorghum, and sugarcane.

Further, the preferred embodiment has involved determining inoculation efficacy of the isolated endophytic bacteria by determining inoculum density in root and shoot of corn and root and shoot of sorghum.

Further, the preferred embodiment has involved using phosphate deficiency symptoms, root/shoot ratio, and chlorophyll content measurements in demonstrating that corn and sorghum seeds inoculated with selected Pi solubilizing endophytic bacteria grown with insoluble mineral-P species present in soils such as rock-phosphate and iron-phosphate performed as well or better than non-inoculated control seeds grown with full strength Hoagland solution containing dissolved P.

FIG. 8 shows healthy and better growth with no soluble/dissolved phosphorus fertilizer in T6 (NRRL accession number B-67827) heterologously inoculated corn seed compared to the control plants (reference plants that are uninoculated) grown with recommended amounts of phosphorus fertilizer. Uninoculated phosphorus deficient plants in comparison show very poor growth.

In FIG. 9, the ~40% reduction in root and shoot lengths in the reference plant in the absence of dissolved phosphorus fertilizer (treatment labeled 1) compared to the reference plant grown with recommended amounts of phosphorus fertilizer (treatment labeled 2) are clearly indicative of the need for dissolved phosphorus fertilizer for optimal plant growth. In FIG. 9, the plant grown from heterologously inoculated corn seed grown in complete absence of any soluble phosphorus fertilizer (see treatments labeled 3 and 4) grew as well or better than the reference plant grown from uninoculated seed with recommended amounts of dissolved phosphorus fertilizer.

FIG. 10 further shows that the plants grown from T6 (NRRL accession number B-67827) heterologously inoculated corn seed in the absence of all dissolved phosphorus fertilizer have the best chlorophyll contents when compared to uninoculated reference plant grown with recommended amounts of dissolved phosphorus fertilizer and also surprisingly when compared to T4 heterologously inoculated corn seed in the absence of all dissolved phosphorus fertilizer.

FIG. 11 shows healthy and better growth with no soluble/dissolved phosphorus fertilizer in T6 (NRRL accession number B-67827) heterologously inoculated sorghum seed compared to the control plants (reference plants that are uninoculated) grown with recommended amounts of phosphorus fertilizer. Uninoculated phosphorus deficient plants in comparison show very poor growth.

In FIG. 12, the ~40% reduction in root length and ~70% reduction in shoot lengths in the reference plant in the absence of dissolved phosphorus fertilizer (treatment labeled 1) compared to the reference plant grown with recommended amounts of phosphorus fertilizer (treatment labeled 2) are clearly indicative of the need for dissolved phosphorus fertilizer for optimal plant growth. In FIG. 12, plant grown from heterologously inoculated sorghum seed grown in complete absence of any soluble phosphorus fertilizer (see treatments labeled 3 and 4) grew as well or better than the reference plant grown from uninoculated seed with recommended amounts of dissolved phosphorus fertilizer.

EXAMPLE 1: ISOLATING ENDOPHYTIC BACTERIA FROM FRESH PLANT SAMPLES

Figure 1:
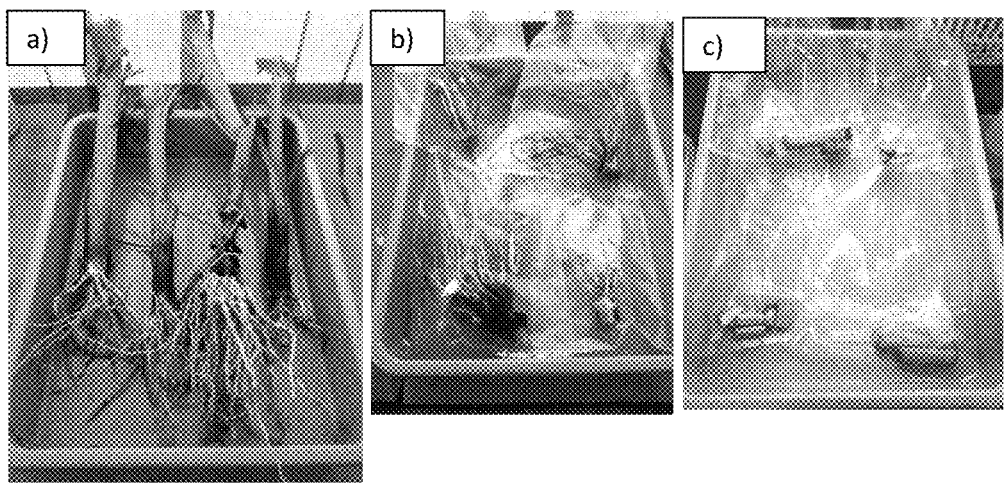
FIG. 1: Endophytic bacteria isolated from plants corn, sorghum, sugarcane: a) corn plants washed in tap water; b) separated roots and shoots; c) separated and chopped corn shoots for further surface sterilization and grinding to isolate endophytic bacteria
Figure 2:
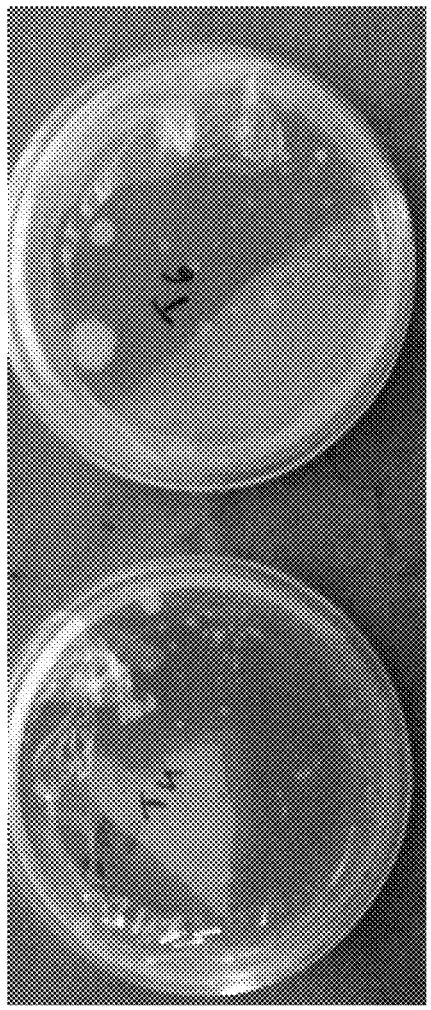
FIG. 2: Endophytic bacteria isolated from corn plants
Figure 2:
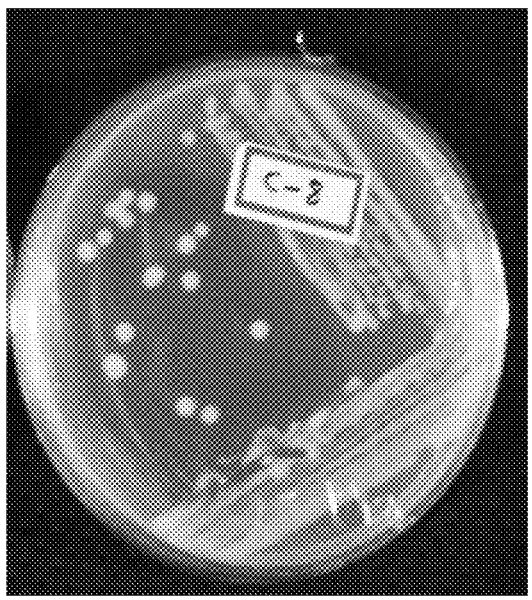
Figure 3:
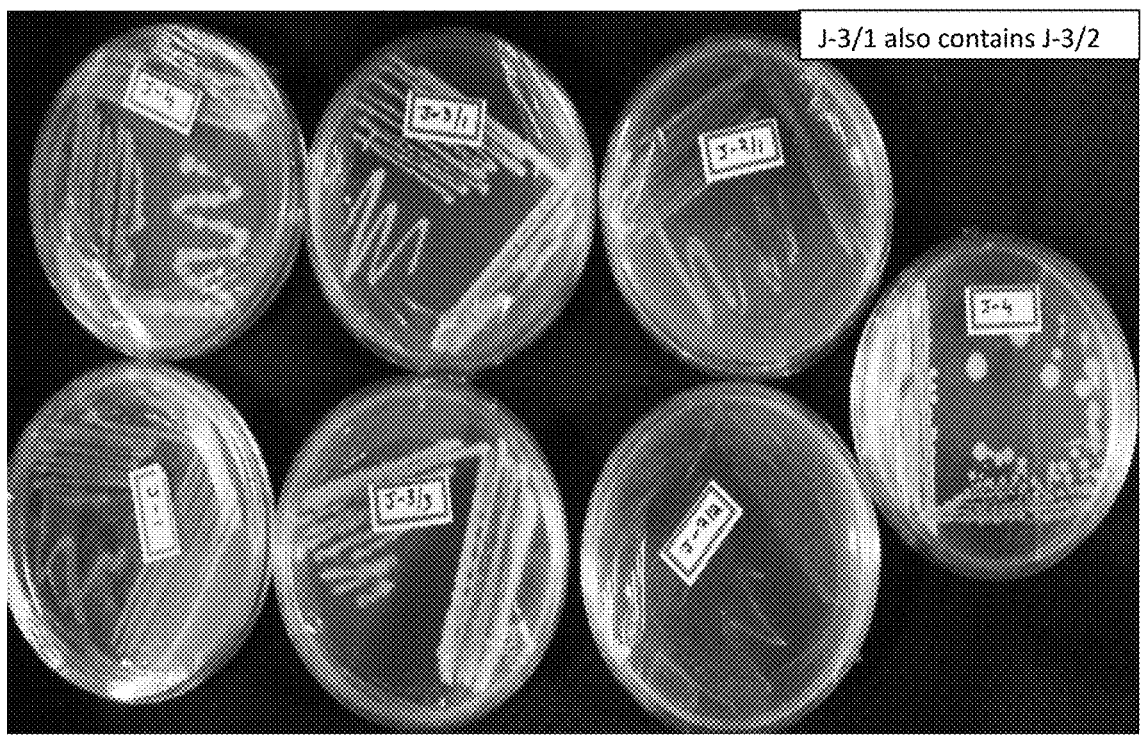
FIG. 3: Endophytic bacteria isolated from sorghum plants
Figure 4:
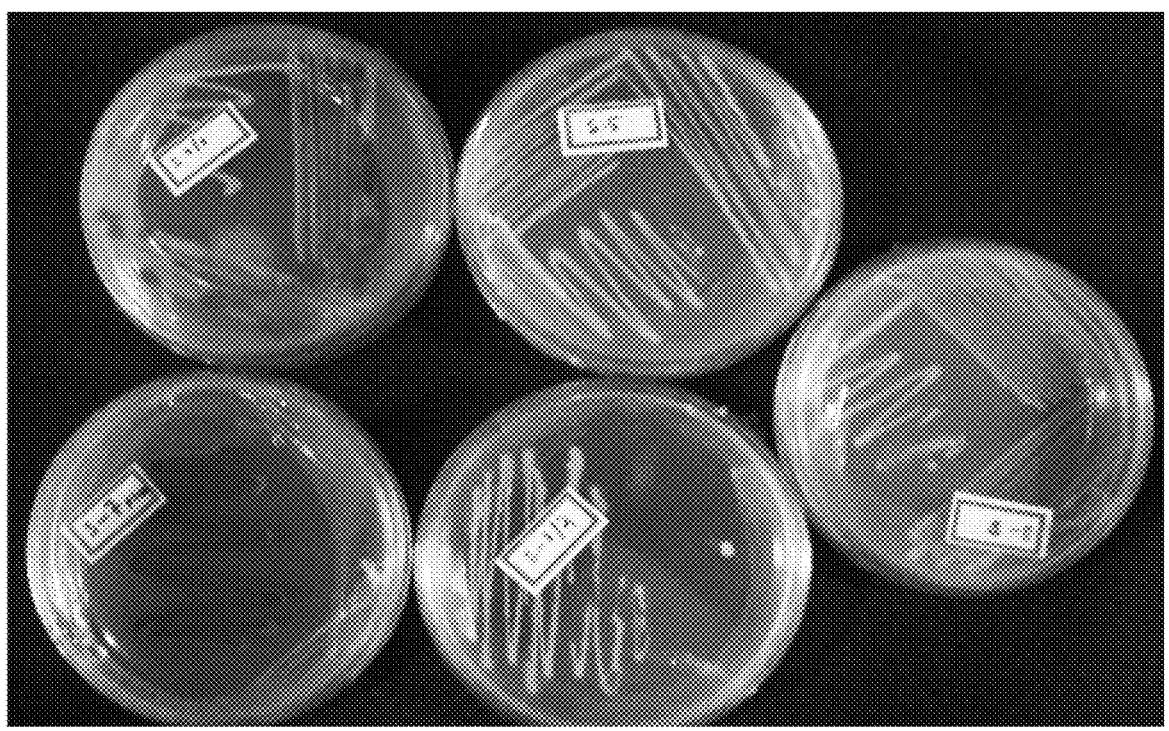
FIG. 4: Endophytic bacteria isolated from sugarcane plants
Figure 5:
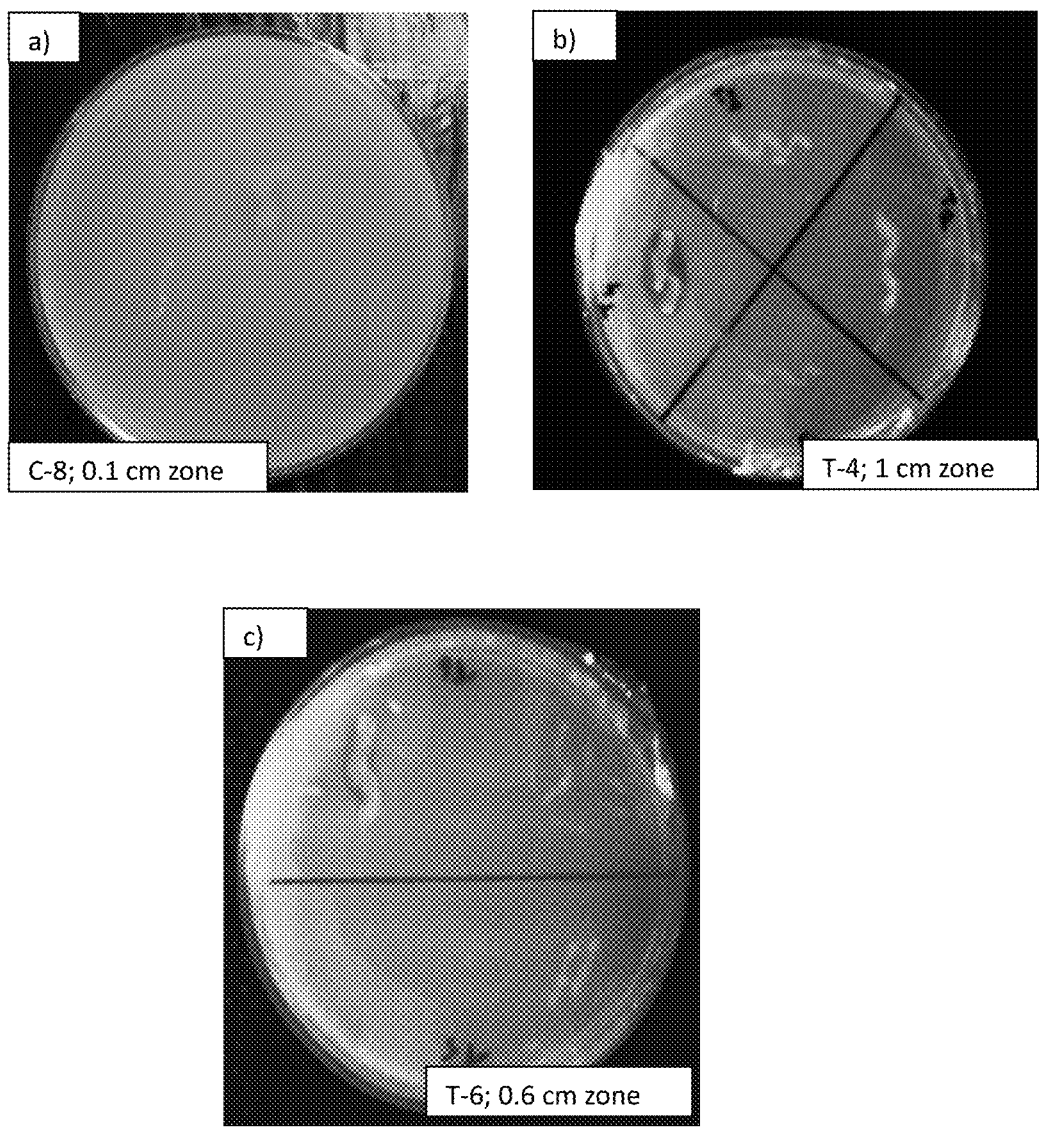
FIG. 5: a), b), and c) showing endophytic bacteria isolated from corn plants that solubilize P; based on sperber's $PO_4$ solubilizing assay
Figure 6:
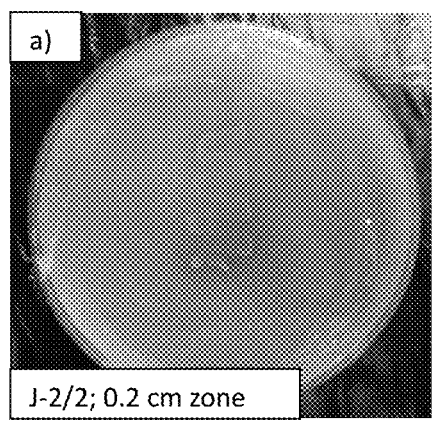
FIG. 6: a), b), and c) showing endophytic bacteria isolated from sorghum plants that solubilize P; based on sperber's $PO_4$ solubilizing assay
Figure 6:
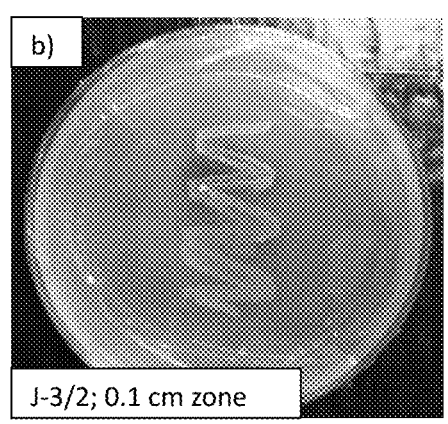
Figure 6:
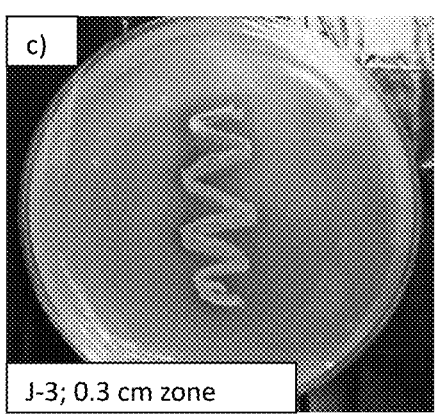
Figure 6:
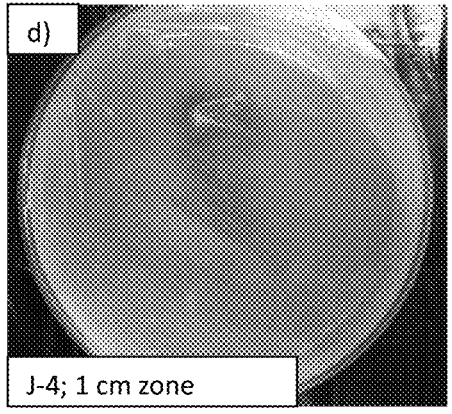
Figure 7:
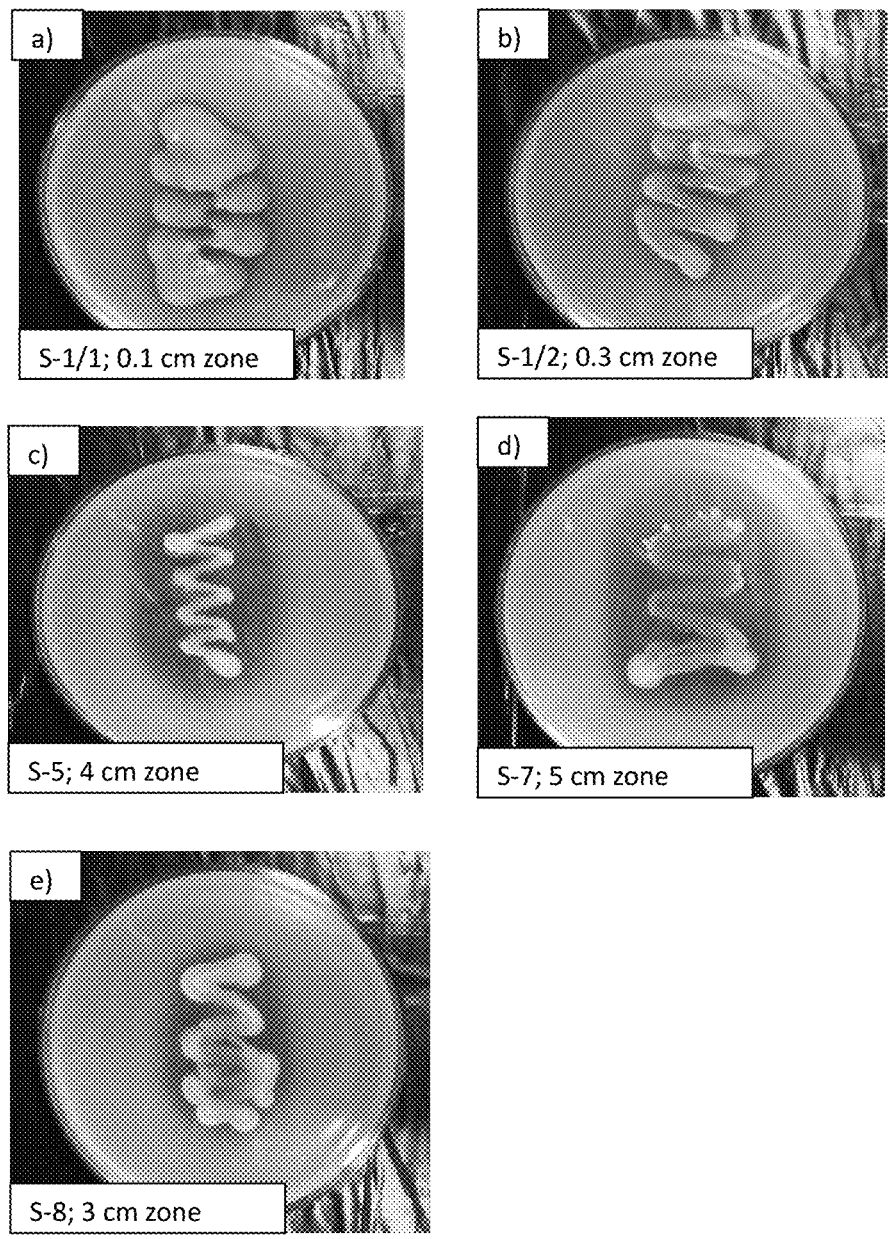
FIG. 7: a), b), and c) showing endophytic bacteria isolated from sugarcane plants that solubilize $P_i$ based on sperber's $PO_4$ solubilizing assay
Figure 8:
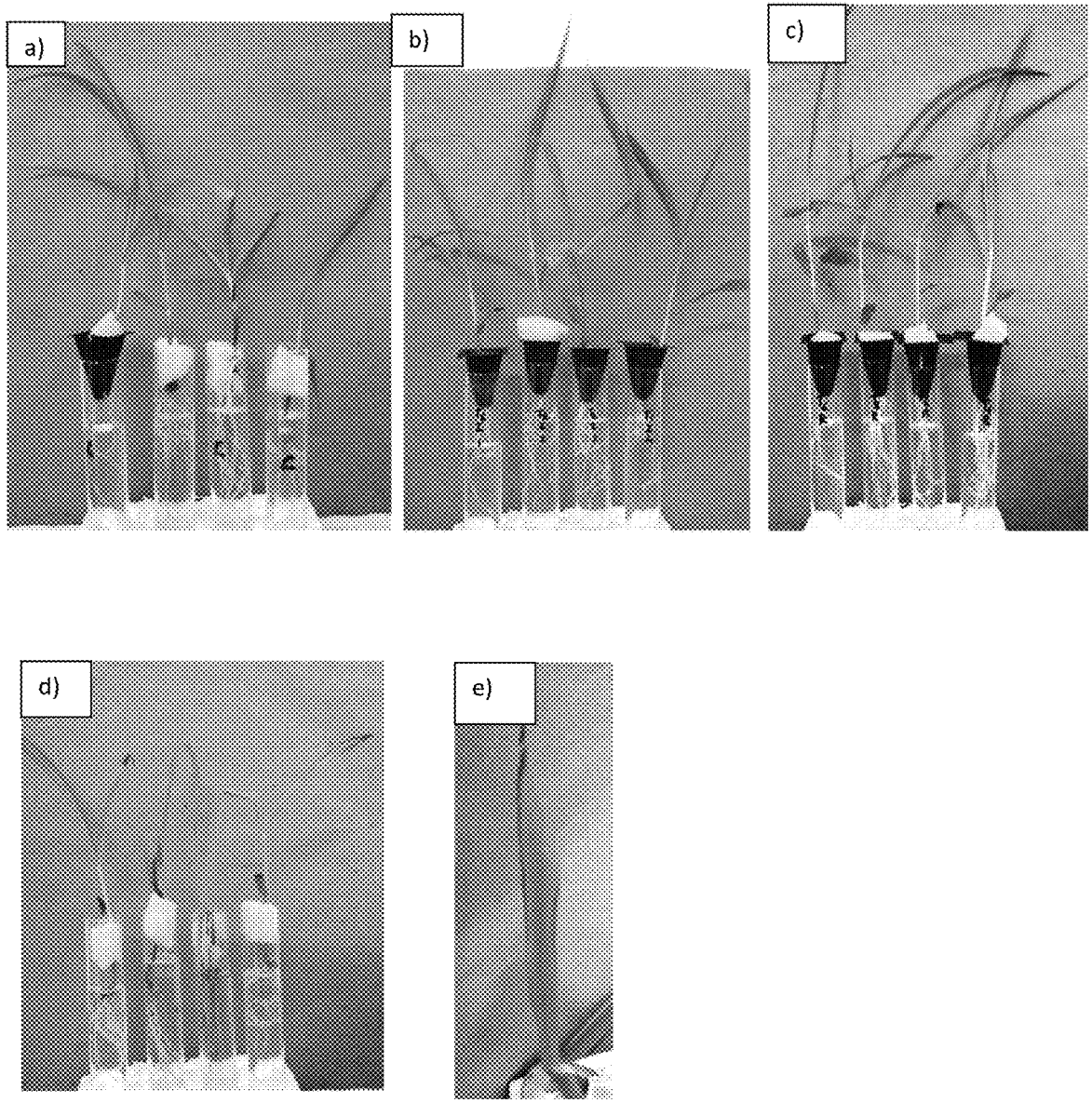
FIG. 8: a) control plants in complete Hoagland solution; b) corn plant inoculated with T6 grown in modified Hoagland solution amended with 0.2 g rock phosphate; c) corn plant inoculated with T6 grown in modified Hoagland solution amended with 0.1 g iron-phosphate; d) and e) non-inoculated corn growing in phosphate deficient Hoagland solution
Figure 9:
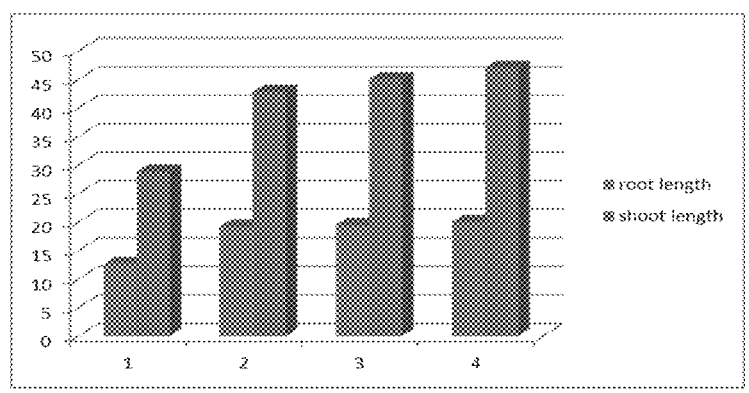
FIG. 9: root and shoot length plotted for 1) control plant grown in phosphate deficient Hoagland solution show very poor growth as measured by their poor root and shoot lengths indicative of yield; 2) corn plant grown in complete Hoagland solution as expected are healthy and show good/optimal root and shoot growth; 3) corn plant grown in phosphate deficient Hoagland solution amended in iron-phosphate nanoparticles show root length and shoot lengths better than the reference/control plants; 4) corn plants grown in phosphate deficient Hoagland solution amended in rock-phosphate also show root length and shoot lengths better than the reference/control plants
Figure 10:
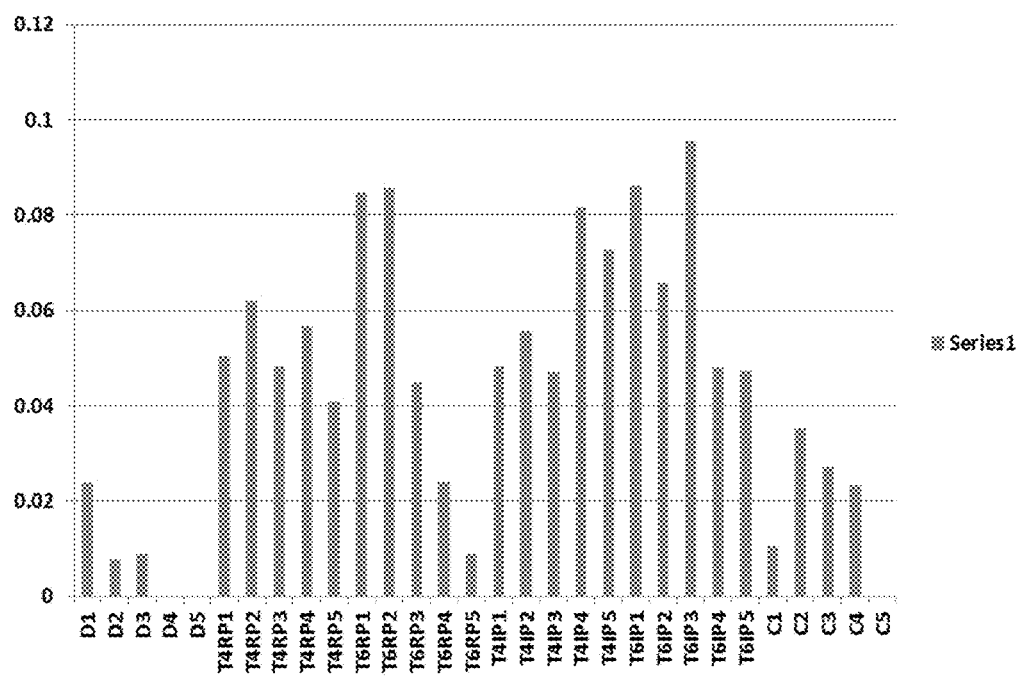
FIG. 10: Total chlorophyll content comparing T6, and T4 inoculated corn grown on rock phosphate (T4RP, T6RP) and iron phosphate, respectively (T4IP, T6IP), and control plants (D) and corn plants grown in full strength Hoagland solution (C)
Figure 11:
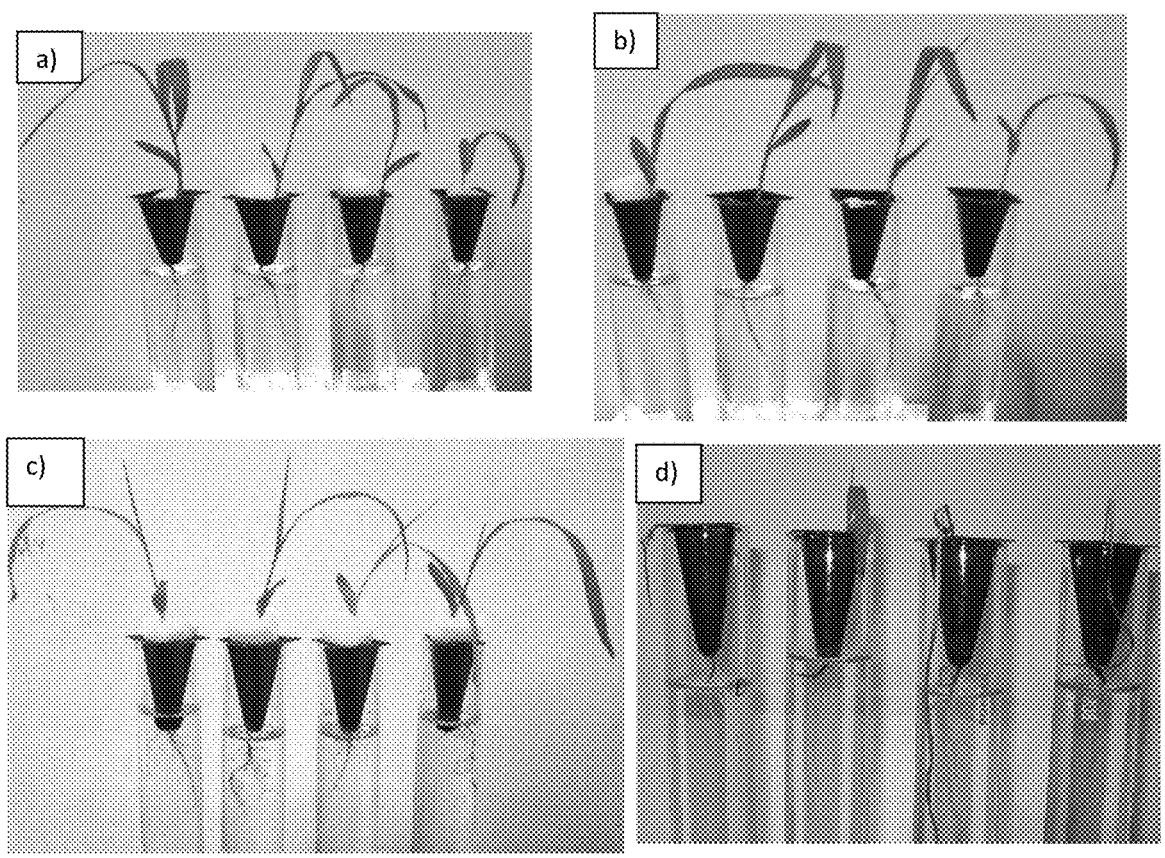
FIG. 11: a) sorghum control plants in complete Hoagland solution; b) sorghum plant inoculated with T6 grown in modified Hoagland solution amended with 0.1 g iron phosphate nanoparticles; c) sorghum plant inoculated with T6 grown in modified Hoagland solution amended with 0.2 g rock-phosphate; d) non-inoculated sorghum growing in phosphate deficient Hoagland solution
Figure 12:
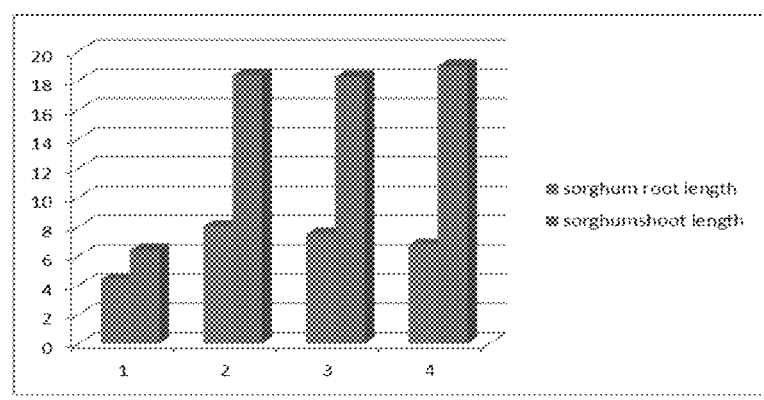
FIG. 12: root and shoot length plotted for 1) control plant grown in phosphate deficient Hoagland solution show very poor growth as measured by their poor root and shoot lengths indicative of yield; 2) sorghum plant grown in complete Hoagland solution as expected are healthy and show good/optimal root and shoot growth; 3) sorghum plant grown in phosphate deficient Hoagland solution amended with iron-phosphate nanoparticles show root length and shoot lengths same as reference/control plants; 4) sorghum plants grown in phosphate deficient Hoagland solution amended with rock-phosphate show root length and shoot lengths slightly better than the reference/control plants.

Fresh samples of corn, sorghum, and sugarcane plants were acquired and washed in tap water.

The roots and shoots from each plant were separated and chopped. They were then surface sterilized to eliminate any epiphytic bacteria and to facilitate isolation of only endophytic bacteria. The samples were then ground to isolate endophytic bacteria. Endophytic bacteria isolated from corn plants included T4, T6, and C8. Endophytic bacteria isolated from sorghum plants included J-1, J-2/1, J-2/2, J-3/1, J-3/2, J-3/3, and J-4. Endophytic bacteria isolated from sugarcane plants included S-1/1, S-1/2, S-5, S-7, and S-8.

EXAMPLE 2: TESTING ENDOPHYTIC BACTERIA FOR INORGANIC-P SOLUBILIZATION

Sperber's media for screening Pi solubilizing endophytic bacteria: The basal Sperber (1958) medium was used and contained glucose 10.0 g/l, yeast extract 0.5 g/l, $CaCl_2$) 0.1 g/l, $MgSO_4.7H_2O$ 0.25 g/l and agar 15.0 g/l. The medium was supplemented with 2.5 g/L of $Ca_3(PO_4)_2$ (TCP-tricalcium phosphate) as P source to appraise the ability of the strains to mobilize inorganic P sources. The pH of the medium was adjusted to 7.2 before autoclaving. The media were distributed in 9 cm diameter Petri plates and marked in four equal parts after solidification. Using the drop plate method, each part was inoculated with innocula. All tests were performed with four replications. Inoculated plates were incubated in dark at 27 degree C. and the diameter of clear zone (halo) surrounding the bacterial growth as well as the diameter of colony were measured after 10, 20 and 30 days.

TABLE 1

Results of Sperber's $PO_4$ solubilizing Assay

| Endophytic bacteria isolated from corn (C, T), surgarcane (S) and sorghum (J) | Phosphate solubilizing activity (zone in cm) |
|---|---|
| C-8 | Very low (0.1 cm) |
| T-4 | Medium (1 cm) |
| T-6 | Medium (0.6 cm) |
| J-2/2 | Very low (0.2 cm) |
| J-3/2 | Very low (0.1 cm) |
| J-3/1 | Very low (0.3 cm) |
| J-4 | Medium (1 cm) |
| S-1/1 | Very low (0.1 cm) |
| S-1/2 | Very low (0.3 cm) |
| S-5 | Very high (4 cm) |
| S-7 | Very high (5 cm) |
| S-8 | High (3 cm) |

EXAMPLE 3: TESTING ENDOPHYTIC BACTERIA FOR ACID PHOSPHATASE PRODUCTION

Screening for acid phosphatase producing endophytic bacteria: The isolated strains were grown in 50 ml of liquid medium (0.1% Ca-phytate; 1.5% glucose; 0.2% $NH_4NO_3$; 0.05% KCl; 0.05% $MgSO_4.7H_2O$; 0.03% $MnSO_4.4H_2O$; 0.03% $FeSO_4.7H_2O$, pH 5.5) in 500-ml flask and incubated at 28 degree C. for 48 hours on reciprocal shaker (200 rpm). The cells were collected from 1 ml of culture by centrifugation at 5000×g for 10 minutes in cool room (40 C) and re-suspended in acetate buffer (0.2 M, pH 5.5). The reaction mixture was prepared. It consisted of 0.8 ml acetate buffer (0.2 M, pH 5.5) containing 1 mM Na-phytate and 0.2 ml of cell suspension. After incubation for 30 minutes at 37 degree C., the reaction was stopped by adding 1 ml of trichloroacetic acid. One ml aliquot was analyzed for inorganic phosphate liberated using the colorimetric procedure. One unit of enzyme activity was defined as the amount of enzyme liberating 1 n mol of inorganic phosphate per minute.

TABLE 2

Results of acid phosphatase assay

| Endophytic bacteria isolated from corn (C, T), surgarcane (S) and sorghum (J) | Concentration of acid phosphatase produced (mg/l) |
|---|---|
| J-1 | 0.60 |
| S-5 | 0.60 |
| C-8 | 0.58 |
| J-4 | 0.57 |
| S-7 | 0.62 |
| J-2/2 | 0.52 |
| T6 | 0.60 |
| J3/1 | 0.62 |
| T4 | 0.61 |
| S-1/2 | 0.60 |
| J-2/1 | 0.59 |

EXAMPLE 4: TESTING ENDOPHYTIC BACTERIA FOR ALKALINE PHOSPHATASE PRODUCTION

Screening for alkaline phosphatase producing endophytic bacteria: The endophytic bacteria were grown in blood agar for 24 h. One colony was transferred and incubated at 37 degree C. in 2.75 ml of propanediol buffer (0.2 mol/liter, pH 7.5) containing 2 mg of 5-bromo-4-chloro-3-indolyl phosphate previously dissolved in 0.25 ml of N,N-dimethyl formamide. 0.2 ml of $MgCl_2$ (5 mmol/liter) was added as an activator. Alkaline phosphatase production was examined every 30 minutes for 4 h by looking for a blue-green indigo precipitate development on the bacterial growth causing the entire solution to become blue.

TABLE 3

Results of alkaline phosphatase assay

| Endophytic bacteria isolated from corn (C, T), surgarcane (S) and sorghum (J) | Change of color to indigo blue-green |
|---|---|
| C-8 | Negative |
| T-4 | Negative |
| T-6 | Positive |
| J-1 | Negative |
| J-2/1 | Negative |
| J-2/2 | Negative |
| J-3/2 | Negative |
| J-3/1 | Negative |
| J-3/3 | Negative |
| J-4 | Negative |
| S-1/1 | Negative |
| S-1/2 | Negative |
| S-5 | Negative |
| S-7 | Negative |
| S-8 | Negative |

EXAMPLE 5: TESTING INOCULATION EFFICACY OF ENDOPHYTIC BACTERIA

The inoculum for endophytic bacteria was grown under controlled conditions for 48 hrs to inoculum density of $10^8$ to $10^{10}$ cfu/ml. The inoculum was centrifuged and suspended in sterile PBS to a concentration of $10^8$ cfu/ml. The seeds were surface sterilized with 95% ethanol for 2 min and 2.5% sodium hypochlorite for 20-30 min followed by washing seven times in sterile water. Surface sterilized seeds were soaked in sterile PBS containing endophytic bacteria and placed in a temperature controlled incubator shaker at 25 degree C. for exactly 30 minutes. The inoculated seeds were washed with 70% alcohol for 2 minutes and with 2% sodium hypochlorite followed by washing with sterile water 5 times. The surface sterilized seeds were placed in sterile petriplates containing 0.7% of water agar, 5-10 seeds per plate. The seed containing plates were transferred to growth chamber set at 30 degree C. and left for 48 hours to germinate. Well germinated seeds with shoot and roots were separated and surface sterilize with 95% of ethanol for 5 min and 20 min with 4% sodium hypochlorite followed by 4-5 times sterile water rinse. The water rinsed root and shoot parts were transferred to PBS containing solution and ground to rapture the tissue. 1 ml of ground tissue was diluted in 9 ml of sterile water serial dilutions were continued to obtain 100 and 1000 fold dilution and spread on nutrient agar plates. After growth the colonies were counted and tabulated. Non-inoculated seeds served as negative controls.

TABLE 4

Inoculation efficacy of endophytic bacteria in corn and sorghum

| Sample description | cfu/ml (calculated using 1000 fold dilution) |
|---|---|
| Corn-root inoculated with T6 | $2.1 \times 10^6$ |
| Corn-shoot inoculated with T6 | $1.7 \times 10^5$ |
| Sorghum-root inoculated with T6 | $2.6 \times 10^6$ |
| Sorghum-shoot inoculated with T6 | $3.4 \times 10^5$ |

Un-inoculated corn and sorghum seeds showed zero inoculum density in roots and shoots EXAMPLE 6: TESTING THE EFFICACY OF ENDOPHYTIC INOCULATION FOR ELIMINATING CHEMICAL FERTILIZERS IN CONTROLLED HYDROPONIC SYSTEMS Standard Hoagland solutions (hydroponic nutrient solutions) were prepared and contained $Ca(NO_3)_2 \cdot 4H_2O$, $NH_4NO_3$, $KCl$, $KNO_3$, $Mg(NO_3)_2 \cdot 6H_2O$, $KH_2PO_4$, $Fe(NO_3)_3 \cdot 9H_2O$, Na HEDTA, $MnCl_2 \cdot 4H_2O$, $H_3BO_3$, $ZnSO_4 \cdot 7H_2O$, $CuSO_4 \cdot 5H_2O$, and $Na_2MoO_4 \cdot 2H_2O$. The young corn seedlings cannot tolerate full strength Hoagland solution. Hence ½ strength Hoagland solution was used from VE to V1 vegetative stage. The plants were grown until V3 vegetative growth stage because phosphate deficiency symptoms can be observed during V1 to V3 growth stage. Phosphate deficient Hoagland solution was prepared by eliminating $KH_2PO_4$.

The viable inoculated seeds were placed in a muslin cloth and washed with running tap water and dried by placing on autoclaved tissue paper. The seeds were surface sterilized in laminar flow hood with 70% alcohol for 30 minutes and then by washing with 10% sodium hypochlorite solution for 20 minutes. After surface sterilization, the seeds were washed with sterile water, excess water removed by blotting with autoclaved tissue paper, and then air dried under laminar flow. Five to ten surface sterilized and dried seeds were then placed in sterile petriplates containing water soaked blotting paper and transferred to growth chamber maintained at 25-27 degree C. and left for 48 hours to germinate. After seeds germinated, they were transferred to hydroponic reactors. Hydroponic systems were maintained under greenhouse conditions at 23-24 degree C., 70% relative humidity, and 12 hours photo-period. Seeds were first grown in full strength Hoagland solution and then transplanted into hydroponic reactors for all the treatments and controls. Five replications were used for all treatments and controls.

Hydroponic reactors constituted of root permeable plastic buckets. Air pump with air controllers were used to provide aeration to the plants in hydroponic systems and all systems were maintained under greenhouse conditions at a temperature of 24±2 degree C. and relative humidity of 70±3%. After control plants showed phosphate deficiency symptoms, the plants were removed from hydroponic reactors and washed under running tap water to completely remove Hoagland solution. The plant was dried with blotting paper while taking care to not damage the roots. The roots were separated from the shoots by using sharp scissors and were weighed to record fresh weight of samples. The root and shoot samples were also dried in the dry air oven at 40 degree C. for 2 days and their dry weight was recorded. The root:shoot ratio of individual plants was calculated and recorded.

Reduced leaf area and degradation of chlorophyll in leaves is also symptomatic of phosphate deficiency so we also measure chlorophyll a and chlorophyll b in plants. A single leaf per plant was used for obtaining 10 leaf discs of 1 cm each and weighed. Five of these leaf discs were placed per tube containing 5 ml of 1:1 ratio of DMSO:acetone and the tubes were placed in the dark overnight to allow chlorophyll leaching. After chlorophyll leaching the solution turns green and the concentration of chlorophyll in leaves is calculated by measuring absorbance at 645, and 663 nm. The total chlorophyll is estimated using the following formulas:

Chlorophyll $II$ $a$ (g/l)=0.0127 $A_{663}$–0.00269 $A_{645}$

Chlorophyll $II$ $b$ (g/l)=0.0029 $A_{663}$–0.00468 $A_{645}$

Total Chlorophyll (g/l)=0.0202 $A_{663}$+0.00802 $A_{645}$

What is claimed is:

1. A method comprising using a plant bacterial endophyte that is heterologous to the seed for the purpose of reducing phosphorus fertilizer requirement for optimal plant growth and yield in organic and conventional agriculture compared to a reference agricultural plant grown under the same conditions with no reduction in phosphorus fertilizer that consists essentially of the following steps: 1) growing an endophytic bacteria having the ability to produce organic acids, acid phosphatase enzyme, and alkaline phosphatase enzyme to a inoculum density of $10^8$ to $10^{10}$ cfu/ml; 2) suspending the said inoculum in sterile phosphate buffer saline medium to a concentration of $10^8$ cfu/ml thereby providing an endophytic inoculum; 3) preparing the corn, sorghum, wheat, rice, and other vegetable, fruit, flower or grass seeds or plant parts by surface sterilizing with 95% ethanol for 2 min and 2.5% sodium hypochlorite for 20-30 min followed by washing seven times in sterile water; 4) soaking the aforementioned surface sterile seeds or plant parts in the said endophytic inoculum of step 2; 5) henceforth placing in a temperature controlled incubator at 25 degree C. for exactly 30 minutes with or without gentle shaking at 40-80 rpm, then washing the thus prepared inoculated seeds or plant part with 70% alcohol for 2 minutes and with 2% sodium hypochlorite followed by washing with sterile water 5 times; 6) treating the said prepared seeds or plant parts of step 5 with other seed treatments and coatings; 7) drying the said seed of step 6 before planting; and 8) planting the said prepared seeds or the said plant part in a plant growth medium with less than the recommended phosphorus fertilizer amount wherein the phosphorous is applied as triple superphosphate, diammonium phosphate, rock phosphate, manure or another form.

2. The method of claim 1, wherein the inoculated plant, plant part or seed is introduced in a plant growth medium in an amount effective to increase the yield of plants grown in said plant growth medium.

3. The method of claim 1, in which said endophytic inoculum, is introduced into a plant growth medium as part of an inoculant composition comprising at least $1\times10^5$ colony forming units of said endophytic inoculum per gram or per milliliter of inoculant composition.

4. The method of claim 1, in which said endophytic inoculum, is introduced into a plant growth medium as part of a treated plant part.

5. The method of claim 4, in which said treated plant part comprises at least $1\times10^5$ colony forming units of said endophytic inoculum per kilogram of plant part.

6. The method of claim 1, in which said endophytic inoculum is introduced into a plant growth medium at a rate of at least $1\times10^5$ colony forming units of said endophytic inoculum per acre of plant growth medium.

7. A The method of claim 1 wherein said endophytic inoculum is applied to plant seeds, one year before said plant seed is planted in a plant growth medium.

8. A method comprising using NRRL B 67827 that is heterologous to the seed for the purpose of reducing phosphorus fertilizer requirement for optimal plant growth and yield in organic and conventional agriculture compared to a reference agricultural plant grown under the same conditions with no reduction in phosphorus fertilizer that includes the following steps: 1) growing NRRL B 67827 having the ability to produce organic acids, acid phosphatase enzyme, and alkaline phosphatase enzyme to a specific inoculum density of $10^8$ to $10^{10}$ cfu/ml; 2) suspending the said inoculum in sterile phosphate buffer saline medium to a concentration of $10^8$ cfu/ml thereby providing an endophytic inoculum; 3) preparing the vegetable, fruit, flower, or grass seed, or plant parts by surface sterilizing with 95% ethanol for 2 min and 2.5% sodium hypochlorite for 20-30 min followed by washing seven times in sterile water; 4) soaking the aforementioned seed or plant parts in the said endophytic inoculum; and 5) henceforth placing in a temperature controlled incubator at 25 degree C. or any other temperature dependent on seed type or plant parts with or without gentle shaking at 40-80 rpm for exactly 30 minutes, then washing the thus prepared inoculated seeds or plant parts with 70% alcohol for 2 minutes and with 2% sodium hypochlorite followed by washing with sterile water 5 times; 6) treating the said prepared seeds or plant parts of step 5 with other seed treatments and coatings; 7) drying the said seed of step 6 before planting; and 8) planting the said prepared seeds or the said plant part in a plant growth medium with less than the recommended phosphorus fertilizer amount wherein the phosphorous is applied as triple superphosphate, diammonium phosphate, rock phosphate, manure or another form.

9. The method of claim 1 in which said endophytic inoculum when applied to the said plant seed or plant growth medium can reduce or eliminate leaching of the applied phosphorus fertilizer in conventional and organic agriculture.

10. The method of claim 8 wherein NRRL B 67827 when applied to the said plant seed or plant growth medium can reduce or eliminate leaching of the applied phosphorus fertilizer in conventional and organic agriculture.

11. The method of claim 8 wherein the inoculated plant, plant part or seed is introduced in a plant growth medium to increase yield with optimal growth.

12. The method of claim 8, in which the said strain NRRL B 67827 is introduced into a plant growth medium as part of an inoculant composition comprising at least $1\times10^5$ colony forming units of NRRL B 67827 per gram or per milliliter of inoculant composition.

13. The method of claim 8, in which the said strain NRRL B 67827 is applied to the said plant seed one year before the said plant seed is planted in a plant growth medium.

\* \* \* \* \*